United States Patent [19]
Bailey et al.

[11] Patent Number: 5,584,629
[45] Date of Patent: Dec. 17, 1996

[54] CONNECTOR FOR MEDICAL IMPLANT

[75] Inventors: A. Gregory Bailey, Alabaster; A. C. Folsom, Jr., Pelham, both of Ala.

[73] Assignee: Crystal Medical Technology, a division of Folsom Metal Products, Inc., Birmingham, Ala.

[21] Appl. No.: 453,628

[22] Filed: May 30, 1995

[51] Int. Cl.⁶ .......................... F16B 35/02; F16B 37/12; A61B 17/56
[52] U.S. Cl. .................. 411/178; 411/383; 411/396; 411/424; 403/334; 606/73
[58] Field of Search ................................ 411/383, 395, 411/396, 402, 178, 411, 424; 403/333, 334, 361; 606/65, 73

[56] References Cited

U.S. PATENT DOCUMENTS

| | | | |
|---|---|---|---|
| 1,552,569 | 9/1925 | Schurman | 403/334 X |
| 3,485,520 | 12/1969 | Alexander | 403/334 |
| 4,293,302 | 10/1981 | Hassler et al. | |
| 4,662,775 | 5/1987 | Faul | 403/361 X |
| 4,960,381 | 10/1990 | Niznick | |
| 5,334,024 | 8/1994 | Niznick | |

OTHER PUBLICATIONS

A brochure for Swede–Vent TL by Dentsply (attached) 15821 Ventura Blvd., Suite 420, Encino, CA 91436.

*Primary Examiner*—Neill R. Wilson
*Attorney, Agent, or Firm*—Veal & Marsh

[57] ABSTRACT

A connection for components in a medical implant assembly utilizes a tapered mating surface on each component with cylindrical splines and flutes formed on each mating surface such that the surfaces are complementary to the extent that the splines of one surface are received in the flutes of the adjacent surface. Each surface is continuous with no discontinuity which would act as a stress raiser or enhance concentration of stress in one locale. The complementary surfaces are urged into registry by a screw connection coaxially through the surfaces.

24 Claims, 3 Drawing Sheets

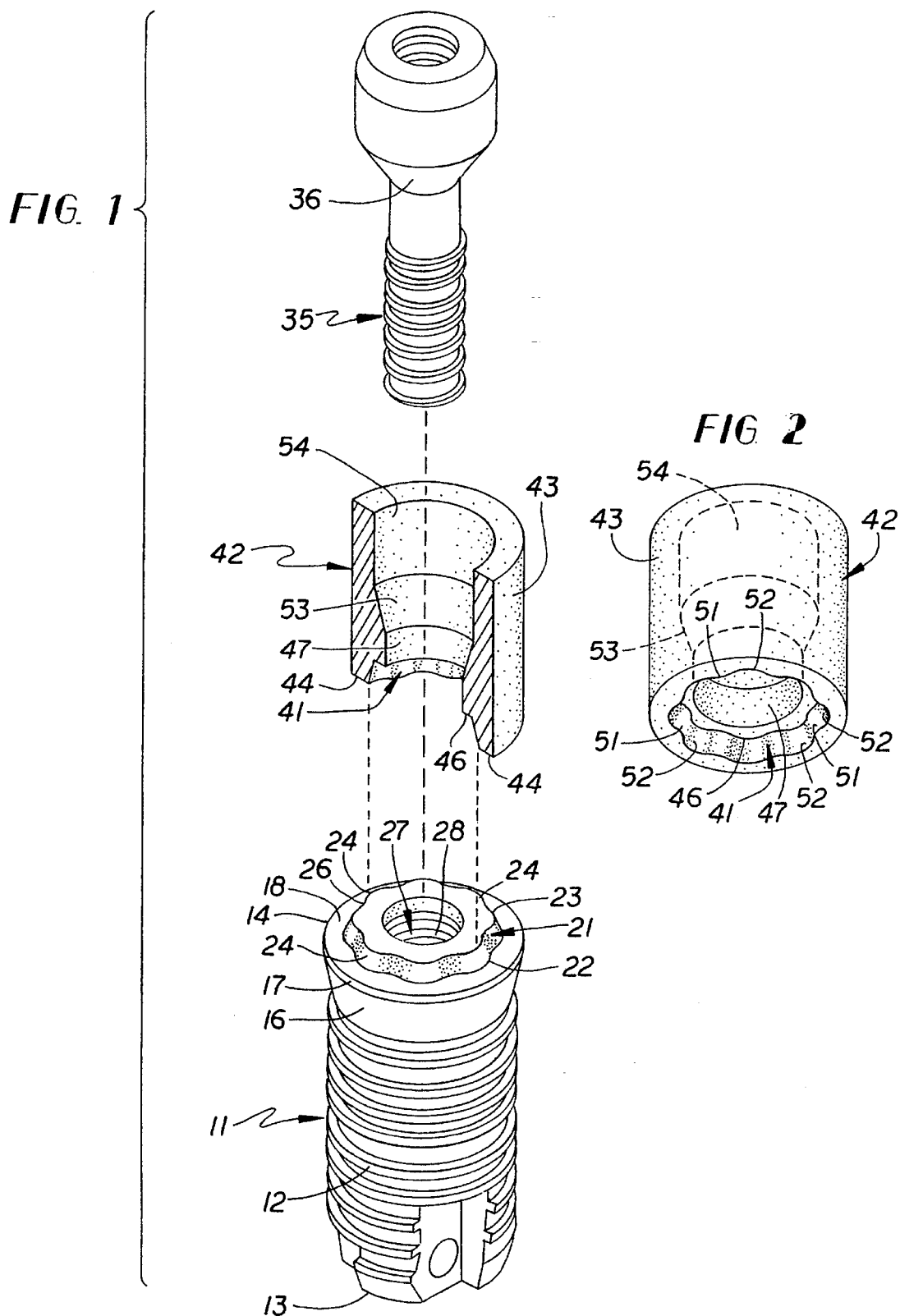

5,584,629

CONNECTOR FOR MEDICAL IMPLANT

FIELD OF THE INVENTION

The present invention relates to the field of medical implant technology, and more particularly to connectors used to connect the components used in medical implant technology. In greater particularity, the present invention relates to a socket configuration which enables indexing of the components and which resists loosening due to torsional loading.

BACKGROUND

Connectors used in implant surgery have used various designs to assemble components together and prevent relative motion between the joined components. Simple tapers have been used for axial alignment and friction lock connections, however, this type of connector is not totally satisfactory. Spalling and fretting generated by motion in the taper as well as complete dislocation of the two bodies due to loss of friction load has been reported. Furthermore, the taper does not provide a means to apply or resist torque, therefore, often times a key is used in conjunction with a tapered shaft. Another type connection used extensively in dental implants is a threaded connection comprising a male hex inserted into a female hex circumscribed about the screw. While this type of connection provides repeatability of registration of location as well as a means to apply or resist torque, it fails to add stability to the connection, since radial clearance must be provided for assembly.

SUMMARY OF THE INVENTION

It is the object of the present invention to provide a fixed index in dental and other medical implants for the mounting of prosthetic devices.

Another object of the invention is to provide an indexable implant abutment which also enhances the stability of the prosthetic device.

Still another object of the invention is to eliminate spalling and fretting of the mating parts.

These and other advantages over the known art are accomplished in the present invention by using a tapered mating surface on each component with cylindrical splines and flutes formed on each mating surface such that the surfaces are complementary to the extent that the splines of one surface are received in the flutes of the adjacent surface. Each surface is continuous with no discontinuity which would act as stress raisers or enhance concentration of stress in one locale. The complementary surfaces are urged into registry by a screw connection coaxially through the surfaces.

BRIEF DESCRIPTION OF THE DRAWINGS

Medical implant devices embodying features of my invention are depicted in the accompanying drawings which form a portion of this disclosure and wherein:

FIG. 1 is an exploded perspective view of a dental implant and prosthesis assembly partially in section;

FIG. 2 is a bottom perspective view of the abutment portion of the implant assembly;

DESCRIPTION OF THE PREFERRED EMBODIMENT

Figure 3:
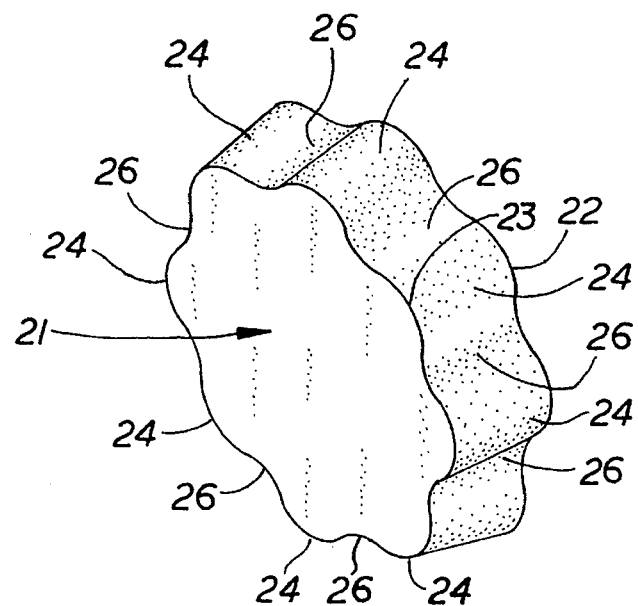
FIG. 3 is a perspective view of the mating surface on an implant.
Figure 4:
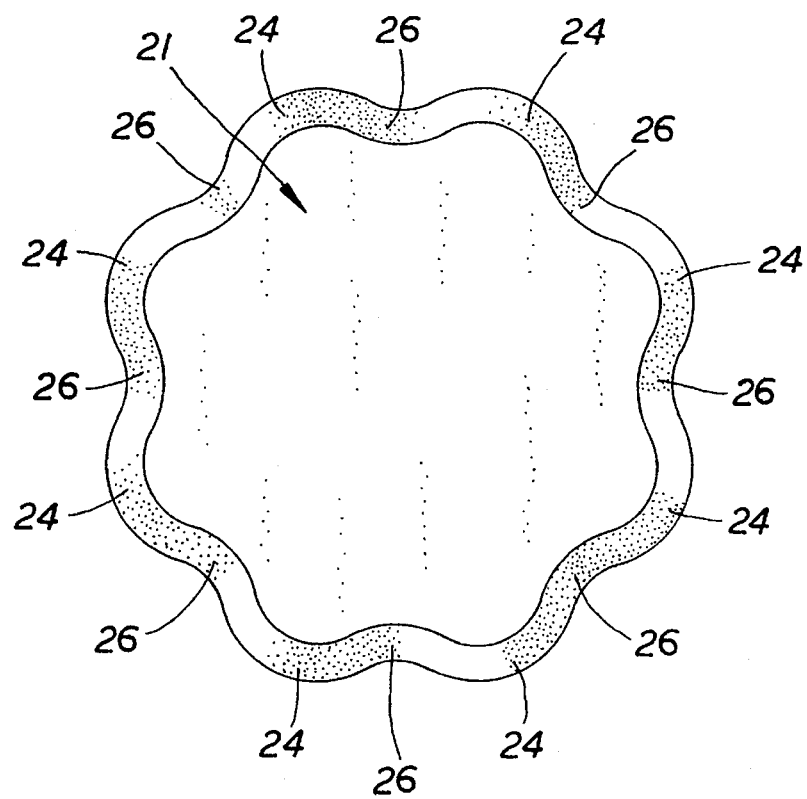
FIG. 4 is a plan view of the mating surface on an implant.
Figure 5:
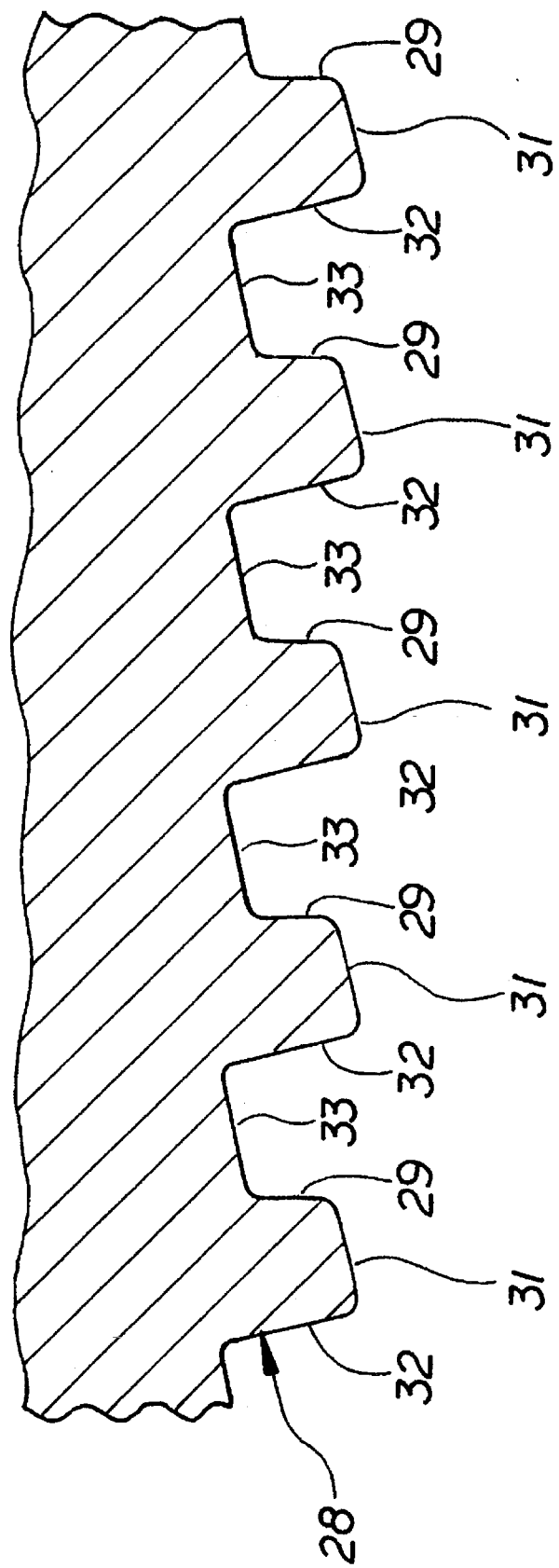
FIG. 5 is a partial sectional view showing the thread profile within the implant.

Referring to the drawings for a clearer understanding of the invention, it may be seen in FIG. 1, that the present invention may be particularly adapted to the field of dental implant prosthetics wherein an implant 11 is osseointegarated into the bone of a patient forming a secure base for the prosthesis. In such an implant, the structure includes a threaded outer surface 12 extending from near an insertion end 13 to proximal an attachment end 14. The insertion end 13 may be configured to be self tapping or tapered to mate with a pre-tapped hole in the bone. The attachment end 14 includes a non-threaded portion 16 of ramped or increasing diameter terminating in a constant diameter annulus 17. A bearing surface 18, perpendicular to the axis of the implant 11 is formed adjacent the constant diameter annulus 17, and circumscribes a truncated cone 21 which tapers from a maximum diameter 22 at the bearing surface 18 to a minimum diameter 23. The cone 21 is machined or otherwise formed, as seen in FIGS. 1–4, such that a plurality of splines 24 and flutes 26 are formed in the cone surface. The splines 24 and flutes 26 are cylindrical such that the surface of the cone 21 has no discontinuities which would serve to increase the stress in any particular area. It may be seen that the cone 21 and bearing surface 18 form a shoulder at the attachment end 14 of the implant. The minor diameter 23 of the cone 21 circumscribes an opening in the implant 11 to a threaded receptacle 27 formed along the axis of the implant 11. The receptacle 27 is formed with a female thread 28, including a load flank 29, crest 31, stab flank 32, and root 33. As may be more clearly seen in FIG. 5, the crest 31 and root 33 are cooperatively formed at an inclined angle rather than being parallel to the axis of the receptacle 27. Threaded fastener 35 has formed thereon a cooperative male thread profile. Consequently, the load flanks do not engage during the make-up of the connection, and the root and crest of the receptacle and fastener move relative to each other without interference until the receptacle and bolt shoulder. This delay in the generation of interference greatly reduces the likelihood of galling.

A cooperative surface is formed in a recess 41 on the abutment 42. As may be seen, the abutment 42 connects the implant 11 to the prosthesis and has a curvilinear outer surface 43 terminating in a lower annular surface 44 which is formed for cooperative engagement with bearing surface 18. Recess 41 is circumscribed by the annular surface 44 and tapers inwardly from the surface 44 to a minor diameter 46. Minor diameter 46 circumscribes an opening 47 through which threaded fastener 35 is inserted for engagement into receptacle 27. Recess 41 is further machined such that the tapered surface has formed thereon a plurality of cooperative splines 51 and flutes 52, which register with the splines 24 and flutes 26 of cone 21. Recess 41 communicates with an axial bore 53 of the abutment 42 through opening 47. Axial bore 53 flares from opening 47 to form a bearing seat 54 which engages an increasing diameter portion 36 of threaded fastener 35. Fastener 35 has a secondary threaded receptacle formed therein for the attachment of the prosthesis.

As may be understood from the forgoing, the mating surfaces of the cone 21 and recess 41 are positioned such that the abutment can be seated with precision relative to the implant 11 which facilitates alignment of the prosthesis. Further, the interaction of the splines and flutes resist torsional loads to eliminate movement of the abutment relative to the implant and do not induce stress raising discontinuities into the interface, thus, torsional loading is not concentrated as may occur with rectangular keys or hex connections.

It will also be appreciated that the splined cone provides a means for applying torque to the implant to seat the implant initially.

While we have shown our invention in one embodiment, it will be obvious to those skilled in the art that it is not so limited but is susceptible of various changes and modifications without departing from the spirit thereof.

What we claim is:

1. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter and an annular shoulder circumscribing said major diameter, wherein said cone circumscribes an opening for a threaded receptacle for a threaded fastener.

2. The improvement as defined in claim 1 wherein said truncated cone is formed on a dental implant and further comprising a conic recess formed in a dental abutment, with said implant and abutment secured to each other with a threaded fastener passing through said opening and engaged within said threaded receptacle.

3. The improvement as defined in claim 1 wherein a mating surface defines a fluted conic recess having a plurality of flutes for cooperatively receiving therein the splines of said cone, said recess flaring from a minor diameter to a major diameter circumscribed by an annular abutment surface which cooperatively mates with said annular shoulder.

4. The improvement as defined in claim 3 wherein said truncated cone is formed on a dental implant and said conic recess is formed on a dental abutment with said implant and abutment secured to each other with a threaded fastener passing through said opening and engaged within said threaded receptacle.

5. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter, an annular shoulder circumscribing said major diameter, and a mating surface defining a fluted conic recess having a plurality of flutes for cooperatively receiving therein the splines of said cone, said recess flaring from a minor diameter to a major diameter circumscribed by an annular abutment surface which cooperatively mates with said annular shoulder, wherein said cone circumscribes an opening for a threaded receptacle for a threaded fastener, wherein said cone is formed on a dental implant and said conic recess is formed on a dental abutment with said implant and abutment secured to each other with a threaded fastener passing through said opening and engaged within said threaded receptacle, wherein said threaded fastener has a thread profile characterized by a root and crest surface defining an inclined helix relative to the centerline of said fastener.

6. The improvement as defined in claim 5, wherein said cone is smoothly splined.

7. The improvement as defined in claim 5 wherein said splined truncated cone has formed thereon at least one cylindrical spline.

8. The improvement as defined in claim 5 wherein said splined truncated cone has a continuous surface with a plurality of cylindrical splines separated by interstitial flutes.

9. The improvement as defined in claim 5 wherein said minor diameter of said conic recess circumscribes an opening cooperatively aligned with said threaded receptacle.

10. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter, an annular shoulder circumscribing said major diameter, and a mating surface defining a fluted conic recess having a plurality of flutes for cooperatively receiving therein the splines of said cone, said recess flaring from a minor diameter to a major diameter circumscribed by an annular abutment surface which cooperatively mates with said annular shoulder, wherein said cone circumscribes an opening for a threaded receptacle for a threaded fastener, wherein said cone is formed on a dental implant and said conic recess is formed on a dental abutment with said implant and abutment secured to each other with a threaded fastener passing through said opening and engaged within said threaded receptacle, wherein said fastener has a thread portion having a maximum diameter less than said opening and a head portion having a larger diameter than said thread portion, said fastener tapering from said head portion to said thread portion, said abutment having an axial bore communicating with said opening, said bore being partially defined by a portion cooperatively tapered to engage the taper of said fastener.

11. The improvement as defined in claim 10, wherein said cone is smoothly splined.

12. The improvement as defined in claim 10, wherein said splined truncated cone has formed thereon at least one cylindrical spline.

13. The improvement as defined in claim 10, wherein said splined truncated cone has a continuous surface with a plurality of cylindrical splines separated by interstitial flutes.

14. The improvement as defined in claim 10, wherein said minor diameter of said conic recess circumscribes an opening cooperatively aligned with said threaded receptacle.

15. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter and an annular shoulder circumscribing said major diameters wherein said cone circumscribes an opening for a threaded receptacle for a threaded fastener, wherein said cone is formed on a dental implant and further comprising a conic recess formed in a dental abutment, said implant and abutment secured to each other with a threaded fastener passing through said opening and engaged within said threaded receptacle, wherein said threaded fastener has a thread profile characterized by a root and crest surface defining an inclined helix relative to the centerline of said fastener.

16. The improvement as defined in claim 15 wherein said conic recess has a plurality of flutes for cooperatively receiving therein said cone, said recess flaring from a minor diameter to a major diameter circumscribed by an annular abutment surface which cooperatively mates with said annular shoulder.

17. The improvement as defined in claim 16 wherein said splined truncated cone and said conic recess each have a continuous surface with a plurality of cylindrical splines separated by interstitial flutes.

18. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter and an annular shoulder circumscribing said major diameter, wherein said cone circumscribes an opening for a threaded receptacle for a threaded fastener, wherein said truncated cone is formed on a dental implant and further comprising a conic recess formed in a dental abutment, said implant and abutment secured to each other with a threaded fastener passing through said opening and engaged within said threaded receptacle, wherein said fastener has a thread portion having a maximum diameter less than said opening and a head portion having a larger diameter than said thread portion, said fastener tapering from said head portion to said thread portion, said abutment having an axial bore communicating with said opening, said bore being partially defined by a portion cooperatively tapered to engage the taper of said fastener.

19. The improvement as defined in claim 18 wherein said conic recess has a plurality of flutes for cooperatively receiving therein said cone, said recess flaring from a minor diameter to a major diameter circumscribed by an annular abutment surface which cooperatively mates with said annular shoulder.

20. The improvement as defined in claim 19 wherein said splined truncated cone and said conic recess each have a continuous surface with a plurality of cylindrical splines separated by interstitial flutes.

21. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter, an annular shoulder circumscribing said major diameter, and a mating surface defining a fluted conic recess having a plurality of flutes for cooperatively receiving therein the splines of said cone, said recess flaring from a minor diameter to a major diameter circumscribed by an annular abutment surface which cooperatively mates with said annular shoulder, wherein said cone circumscribes an opening for a threaded receptacle for a threaded fastener, wherein said cone is formed on a medical implant and said conic recess is formed on an abutment with said implant and abutment secured to each other with a threaded fastener passing through said opening and engaged within said threaded receptacle, wherein said threaded fastener has a thread profile characterized by a root and crest surface defining an inclined helix relative to the centerline of said fastener.

22. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter, an annular shoulder circumscribing said major diameter, and a mating surface defining a fluted conic recess having a plurality of flutes for cooperatively receiving therein the splines of said cone, said recess flaring from a minor diameter to a major diameter circumscribed by an annular abutment surface which cooperatively mates with said annular shoulder, wherein said cone circumscribes an opening for a threaded receptacle for a threaded fastener, wherein said cone is formed on a medical implant and said conic recess is formed on an abutment with said implant and abutment secured to each other with a threaded fastener passing through said opening and engaged within said threaded receptacle, wherein said fastener has a thread portion having a maximum diameter less than said opening and a head portion having a larger diameter than said thread portion, said fastener tapering from said head portion to said thread portion, said abutment having an axial bore communicating with said opening, said bore being partially defined by a portion cooperatively tapered to engage the taper of said fastener.

23. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter and an annular shoulder circumscribing said major diameter, wherein said cone circumscribes an opening for a threaded receptacle for a threaded fastener, wherein said cone is formed on a medical implant and further comprising a conic recess formed in an abutment, said implant and abutment secured to each other with a threaded fastener passing through said opening and engaged within said threaded receptacle, wherein said threaded fastener has a thread profile characterized by a root and crest surface defining an inclined helix relative to the centerline of said fastener.

24. An improvement in the connection between mating components in medical implants wherein said components are subjected to torsional loads, comprising an interface defining a mating relationship between adjacent surfaces of said components wherein one of said surfaces defines a splined truncated cone tapering from a major diameter to a minor diameter and an annular shoulder circumscribing said major diameter, wherein said cone circumscribes an opening for a threaded receptacle for a threaded fastener, wherein said truncated cone is formed on a medical implant and further comprising a conic recess formed in an abutment, said implant and abutment secured to each other with a threaded fastener passing through said opening and engaged within said threaded receptacle, wherein said fastener has a thread portion having a maximum diameter less than said opening and a head portion having a larger diameter than said thread portion, said fastener tapering from said head portion to said thread portion, said abutment having an axial bore communicating with said opening, said bore being partially defined by a portion cooperatively tapered to engage the taper of said fastener.

* * * * *